(12) United States Patent
Tanaka

(10) Patent No.: US 9,044,278 B2
(45) Date of Patent: Jun. 2, 2015

(54) INTER SPINOUS PROCESS SPACER WITH COMPRESSIBLE CORE PROVIDING DYNAMIC STABILIZATION

(75) Inventor: Shigeru Tanaka, Half Moon Bay, CA (US)

(73) Assignee: SPINAL KINETICS INC., Sunnyvale, CA (US)

( * ) Notice: Subject to any disclaimer, the term of this patent is extended or adjusted under 35 U.S.C. 154(b) by 934 days.

(21) Appl. No.: 12/266,319

(22) Filed: Nov. 6, 2008

(65) Prior Publication Data

US 2010/0249840 A1    Sep. 30, 2010

(51) Int. Cl.
*A61B 17/70* (2006.01)
*A61F 2/44* (2006.01)
*A61F 2/30* (2006.01)

(52) U.S. Cl.
CPC ......... *A61B 17/7068* (2013.01); *A61B 17/7062* (2013.01); *A61F 2/4405* (2013.01); *A61F 2/441* (2013.01); *A61F 2/442* (2013.01); *A61F 2002/30006* (2013.01); *A61F 2002/30115* (2013.01); *A61F 2002/30126* (2013.01); *A61F 2002/30153* (2013.01); *A61F 2002/30225* (2013.01); *A61F 2002/30228* (2013.01); *A61F 2002/30265* (2013.01); *A61F 2002/30388* (2013.01); *A61F 2002/30462* (2013.01); *A61F 2002/30538* (2013.01); *A61F 2002/3055* (2013.01); *A61F 2002/30553* (2013.01); *A61F 2002/30563* (2013.01); *A61F 2002/30594* (2013.01); *A61F 2002/30616* (2013.01); *A61F 2002/30841* (2013.01); *A61F 2002/30878* (2013.01); *A61F 2002/443* (2013.01); *A61F 2002/444* (2013.01); *A61F 2002/4495* (2013.01); *A61F 2220/0025* (2013.01); *A61F 2220/0075* (2013.01); *A61F 2230/0006* (2013.01); *A61F 2230/0008* (2013.01); *A61F 2230/0019* (2013.01); *A61F 2230/0069* (2013.01); *A61F 2230/0082* (2013.01); *A61F 2250/0006* (2013.01); *A61F 2250/0007* (2013.01); *A61F 2250/0008* (2013.01); *A61F 2250/0015* (2013.01); *A61F 2250/0018* (2013.01); *A61F 2310/00017* (2013.01); *A61F 2310/00023* (2013.01); *A61F 2310/00029* (2013.01);

(Continued)

(58) Field of Classification Search
CPC .................................................... A61F 2/4405
USPC ................... 606/246–249; 623/17.11–17.16
See application file for complete search history.

(56) References Cited

U.S. PATENT DOCUMENTS 3,867,728 A   2/1975  Stubstad
4,932,969 A   6/1990  Frey et al.

(Continued)

OTHER PUBLICATIONS

WO PCT/US2009/062361 Search Report and Written Opinion, Dec. 17, 2009.

(Continued)

*Primary Examiner* — Jan Christopher Merene
(74) *Attorney, Agent, or Firm* — E. Thomas Wheelock

(57) ABSTRACT

The described devices are useful in the treatment of spinal disorders and pain. In particular, the described devices are designed to stabilize a portion of the spine by restoring and maintaining spacing between two adjacent vertebrae. The devices are compressible spacers that may be situated between the spinous processes of those adjacent vertebrae. The described inter spinous process spacers also allow a range of spinal motion and mimic the motion of a normally functioning spine.

9 Claims, 11 Drawing Sheets

(52) U.S. Cl.
CPC ............... *A61F2310/00173* (2013.01); *A61F 2310/00179* (2013.01)

(56) References Cited

U.S. PATENT DOCUMENTS

| | | | |
|---|---|---|---|
| 5,071,437 A | 12/1991 | Steffee | |
| 5,171,281 A | 12/1992 | Parsons et al. | |
| 5,370,697 A | 12/1994 | Baumgartner | |
| 5,645,599 A * | 7/1997 | Samani | 623/17.16 |
| 6,626,943 B2 | 9/2003 | Eberlin et al. | |
| 6,645,248 B2 | 11/2003 | Casutt | |
| 6,733,532 B1 | 5/2004 | Gauchet et al. | |
| 7,563,284 B2 | 7/2009 | Coppes et al. | |
| 7,682,376 B2 * | 3/2010 | Trieu | 606/248 |
| 7,905,921 B2 * | 3/2011 | Kim et al. | 623/17.16 |
| 2002/0147449 A1 | 10/2002 | Yun | 606/61 |
| 2004/0106995 A1 * | 6/2004 | Le Couedic et al. | 623/17.11 |
| 2005/0060034 A1 * | 3/2005 | Berry et al. | 623/17.11 |
| 2005/0165486 A1 * | 7/2005 | Trieu | 623/17.13 |
| 2005/0203624 A1 * | 9/2005 | Serhan et al. | 623/17.11 |
| 2005/0228500 A1 * | 10/2005 | Kim et al. | 623/17.13 |
| 2006/0041313 A1 * | 2/2006 | Allard et al. | 623/17.15 |
| 2006/0241614 A1 * | 10/2006 | Bruneau et al. | 606/69 |
| 2006/0271044 A1 * | 11/2006 | Petrini et al. | 606/61 |
| 2006/0271055 A1 * | 11/2006 | Thramann | 606/74 |
| 2006/0293662 A1 * | 12/2006 | Boyer et al. | 606/61 |
| 2007/0167947 A1 | 7/2007 | Gittings | |
| 2007/0168035 A1 | 7/2007 | Koske | |
| 2007/0191948 A1 * | 8/2007 | Arnin et al. | 623/17.11 |
| 2007/0191959 A1 * | 8/2007 | Hartmann et al. | 623/17.16 |
| 2007/0276500 A1 * | 11/2007 | Zucherman et al. | 623/17.16 |
| 2008/0183209 A1 | 7/2008 | Robinson et al. | |
| 2008/0200986 A1 | 8/2008 | Kim et al. | |
| 2008/0294200 A1 * | 11/2008 | Kohm et al. | 606/279 |
| 2008/0319487 A1 * | 12/2008 | Fielding et al. | 606/263 |
| 2009/0005819 A1 * | 1/2009 | Ben-Mokhtar et al. | 606/249 |

OTHER PUBLICATIONS

Spinal Kinetics, Inc.'s Preliminary Invalidity Contentions (USDC, Case No. 5:09-cv-01201, *Synthes USA et al.* v. *Spinal Kinetics, Inc.*, Sep. 8, 2009).
Spinal Kinetics, Inc.'s Preliminary Invalidity Contentions—Exhibit 1 (chart comparing claims of USP 7,429,270 to Stubstad USP 3,867,728).
Spinal Kinetics, Inc.'s Preliminary Invalidity Contentions—Exhibit 2 (chart comparing claims of USP 7,429,270 to Baumgartner USP 5,370,697 in view of Stubstad USP 3,867,728 and Steffee USP 5,071,437).
Spinal Kinetics, Inc.'s Preliminary Invalidity Contentions—Exhibit 3 (chart comparing claims of USP 7,429,270 to Baumgartner USP 5,370,697 in view of Stubstad USP 3,867,728 and Parsons USP 5,171,281).
Spinal Kinetics, Inc.'s Preliminary Invalidity Contentions—Exhibit 4 (chart comparing claims of USP 7,429,270 to Baumgartner USP 5,370,697 in view of Stubstad USP 3,867,728 and Eberlein USP 6,626,943).
Spinal Kinetics, Inc.'s Preliminary Invalidity Contentions—Exhibit 5 (chart comparing claims of USP 7,429,270 to Baumgartner USP 5,370,697 in view of Stubstad USP 3,867,728 and Casutt USP 6,645,248).
Spinal Kinetics, Inc.'s Preliminary Invalidity Contentions—Exhibit 6 (chart comparing claims of USP 7,429,270 to Baumgartner USP 5,370,697 in view of Stubstad USP 3,867,728 and Frey USP 4,932,969).
Spinal Kinetics, Inc.'s Preliminary Invalidity Contentions —Exhibit 7 (chart comparing claims of USP 7,429,270 to Baumgartner USP 5,370,697 in view of Stubstad USP 3,867,728 and Gauchet USP 6,733,532).
Spinal Kinetics, Inc.'s Preliminary Invalidity Contentions—Exhibit 8 (chart comparing claims of USP 7,429,270 to Baumgartner USP 5,370,697 in view of Stubstad USP 3,867,728 and Development and Characterization of a Prosthetic Intervertebral Disc, Robert Hudgins, Georgia Inst. of Tech., Nov. 1998).
Spinal Kinetics, Inc.'s Preliminary Invalidity Contentions —Exhibit 9 (chart comparing claims of USP 7,429,270 to Stubstad USP 3,867,728 in view of Baumgartner USP 5,370,697).
Spinal Kinetics, Inc.'s Preliminary Invalidity Contentions—Exhibit 10 (chart comparing claims of USP 7,429,270 to Baumgartner USP 5,370,697 in view of Stubstad USP 3,867,728 and Steffe USP 4,071,437).
Spinal Kinetics, Inc.'s Preliminary Invalidity Contentions—Exhibit 11 (chart comparing claims of USP 7,429,270 to Baumgartner USP 5,370,697 in view of Stubstad USP 3,867,728 and Casutt USP 6,645,248).
Spinal Kinetics, Inc.'s Preliminary Invalidity Contentions—Exhibit 12 (chart comparing claims of USP 7,429,270 to Stubstad USP 3,867,728 in view of Development and Characterization of a Prosthetic Intervertebral Disc, Robert Hudgins, Georgia Inst. of Tech., Nov. 1998).
Spinal Kinetics, Inc.'s Preliminary Invalidity Contentions [Amended] (USDC, Case No. 5:09-cv-01201, *Synthes USA et al.* v. *Spinal Kinetics, Inc.*, Dec. 28, 2009).
Spinal Kinetics, Inc.'s Preliminary Invalidity Contentions [Amended]—Exhibit 1 (chart comparing claims of USP 7,429,270 to Stubstad USP 3,867,728).
Spinal Kinetics, Inc.'s Preliminary Invalidity Contentions [Amended]—Exhibit 2 (chart comparing claims of USP 7,429,270 to Coppes USP 7,563,284).
Spinal Kinetics, Inc.'s Preliminary Invalidity Contentions [Amended]—Exhibit 3 (chart comparing claims of USP 7,429,270 to Coppes USP 7,563,284 in combination with Stubstad USP 3,867,728).
Spinal Kinetics, Inc.'s Preliminary Invalidity Contentions [Amended]—Exhibit 4 (chart comparing claims of USP 7,429,270 to Baumgartner USP 5,370,697 in view of Stubstad USP 3,867,728 and Steffee USP 5,071,437).
Spinal Kinetics, Inc.'s Preliminary Invalidity Contentions [Amended]—Exhibit 5 (chart comparing claims of USP 7,429,270 to Baumgartner USP 5,370,697 in view of Stubstad USP 3,867,728 and Parsons USP 5,171,281).
Spinal Kinetics, Inc.'s Preliminary Invalidity Contentions [Amended]—Exhibit 6 (chart comparing claims of USP 7,429,270 to Baumgartner USP 5,370,697 in view of Stubstad USP 3,867,728 and Eberlein USP 6,626,943).
Spinal Kinetics, Inc.'s Preliminary Invalidity Contentions [Amended]—Exhibit 7 (chart comparing claims of USP 7,429,270 to Baumgartner USP 5,370,697 in view of Stubstad USP 3,867,728 and Casutt USP 6,645,248).
Spinal Kinetics, Inc.'s Preliminary Invalidity Contentions [Amended]—Exhibit 8 (chart comparing claims of USP 7,429,270 to Baumgartner USP 5,370,697 in view of Stubstad USP 3,867,728 and Frey USP 4,932,969).
Spinal Kinetics, Inc.'s Preliminary Invalidity Contentions [Amended]—Exhibit 9 (chart comparing claims of USP 7,429,270 to Baumgartner USP 5,370,697 in view of Stubstad USP 3,867,728 and Gauchet USP 6,733,532).
Spinal Kinetics, Inc.'s Preliminary Invalidity Contentions [Amended]—Exhibit 10 (chart comparing claims of USP 7,429,270 to Baumgartner USP 5,370,697 in view of Stubstad USP 3,867,728 and Development and Characterization of a Prosthetic Intervertebral Disc, Hudgins, Georgia Inst. of Tech., Nov. 1998).
Spinal Kinetics, Inc.'s Preliminary Invalidity Contentions [Amended]—Exhibit 11 (chart comparing claims of USP 7,429,270 to Stubstad USP 3,867,728 in view of Baumgartner USP 5,370,697).
Spinal Kinetics, Inc.'s Preliminary Invalidity Contentions [Amended]—Exhibit 12 (chart comparing claims of USP 7,429,270 to Baumgartner USP 5,370,697 in view of Stubstad USP 3,867,728 and Steffee USP 4,071,437).
Spinal Kinetics, Inc.'s Preliminary Invalidity Contentions [Amended]—Exhibit 13 (chart comparing claims of USP 7,429,270 to Baumgartner USP 5,370,697 in view of Stubstad USP 3,867,728 and Casutt USP 6,645,248).

(56) References Cited

OTHER PUBLICATIONS

Spinal Kinetics, Inc.'s Preliminary Invalidity Contentions [Amended]—Exhibit 14 (chart comparing claims of USP 7,429,270 to Stubstad USP 3,867,728 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions (USDC, Case No. 5:09-cv01201, *Synthes USA et al.* v. *Spinal Kinetics, Inc.*, Sep. 30, 2010).
Spinal Kinetics, Inc.'s Second Amended Preliminary Invalidity Contentions—Exhibit 1 (chart comparing claims of USP 7,429,270 to Neuentwicklung eines Implantates für den totalen Bandschiebenersatz, Vorgelegt von: Adrian Burn und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 2 (chart comparing claims of USP 7,429,270 to Neuentwicklung eines lumbalen bewegungserhaltenden Bandscheibenimplantates, Feb. 25, 2002).
Spinal Kinetics, Inc.'s Second Amended Preliminary Invalidity Contentions—Exhibit 3 (chart comparing claims of USP 7,429,270 to Stubstad USP 3,867,728).
Spinal Kinetics, Inc.'s Second Amended Preliminary Invalidity Contentions—Exhibit 4 (chart comparing claims of USP 7,429,270 to Baumgartner PCT/CH2003/00247).
Spinal Kinetics, Inc.'s Second Amended Preliminary Invalidity Contentions—Exhibit 5 (chart comparing claims of USP 7,429,270 to Neuentwicklung eines Implantates fur den totalen Bandschiebenersatz, Vorgelegt von: Adrian Burn und Daniel Baumgartner Im Rahmen des Studiums für "Maschinenbau und Vergahrenstechnik" an der Eidgenöossischen Technischen Hochschule Zürich, im Februar 2002).
Spinal Kinetics, Inc.'s Second Amended Preliminary Invalidity Contentions—Exhibit 6 (chart comparing claims of USP 7,429,270 to Neuentwicklung eines Implantates für den totalen Bandschiebenersatz, Vorgelegt von: Adrian Burn und Daniel Baumgartner Im Rahmen des Studiums für "Maschinenbau und Vergahrenstechnik" an der Eidgenöossischen Technischen Hochschule Zürich, im Feb. 2002).
Spinal Kinetics, Inc.'s Second Amended Preliminary Invalidity Contentions—Exhibit 7 (chart comparing claims of USP 7,429,270 to Stubstad USP 3,867,728 in view of Eberlein USP 6,626,943).
Spinal Kinetics, Inc.'s Second Amended Preliminary Invalidity Contentions—Exhibit 8 (chart comparing claims of USP 7,429,270 to Stubstad 3,867,728 in view of Kim USP 7,153,325).
Spinal Kinetics, Inc.'s Second Amended Preliminary Invalidity Contentions—Exhibit 9 (chart comparing claims of USP 7,429,270 to Stubstad USP 3,867,728 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 10 (chart comparing claims of USP 7,429,270 to Stubstad 3,867,728 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 11 (chart comparing claims of USP 7,429,270 to Coppes USP 7,563,284 to Stubstad USP 3,867,728).
Spinal Kinetics, Inc.'s Second Amended Preliminary Invalidity Contentions—Exhibit 12 (chart comparing claims of USP 7,429,270 to Coppes USP 7,563,284 in view of Eberlein USP 6,626,943).
Spinal Kinetics, Inc.'s Second Amended Preliminary Invalidity Contentions—Exhibit 13 (chart comparing claims of USP 7,429,270 to Coppes USP 7,563,284 in view of Kim USP 7,153,325).
Spinal Kinetics, Inc.'s Second Amended Preliminary Invalidity Contentions—Exhibit 14 (chart comparing claims of USP 7,429,270 to Coppes USP 7,563,284 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 15 (chart comparing claims of USP 7,429,270 to Coppes USP 7,563,284 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 16 (chart comparing claims of USP 7,429,270 to Baumgartner USP 5,370,697 in view of Stubstad USP 3,867,728).
Spinal Kinetics, Inc.'s Second Amended Preliminary Invalidity Contentions—Exhibit 17 (chart comparing claims of USP 7,429,270 to Baumgartner USP 5,370,697 in view of Eberlein USP 6,626,943).
Spinal Kinetics, Inc.'s Second Amended Preliminary Invalidity Contentions—Exhibit 18 (chart comparing claims of USP 7,429,270 to Baumgartner USP 5,370,697 in view of Kim USP 7,153,325).
Spinal Kinetics, Inc.'s Second Amended Preliminary Invalidity Contentions—Exhibit 19 (chart comparing claims of USP 7,429,270 to Baumgartner USP 5,370,697 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 20 (chart comparing claims of USP 7,429,270 to Baumgartner USP 5,370,697 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 21 (chart comparing claims of USP 7,429,270 to Gauchet USP 6,733,532 in view of Stubstad USP 3,867,728).
Spinal Kinetics, Inc.'s Second Amended Preliminary Invalidity Contentions—Exhibit 22 (chart comparing claims of USP 7,429,270 to Gauchet USP 6,733,532 in view of Eberlein USP 6,626,943).
Spinal Kinetics, Inc.'s Second Amended Preliminary Invalidity Contentions—Exhibit 23 (chart comparing claims of USP 7,429,270 to Gauchet USP 6,733,532 in view of Kim USP 7,153,325).
Spinal Kinetics, Inc.'s Second Amended Preliminary Invalidity Contentions—Exhibit 24 (chart comparing claims of USP 7,429,270 to Gauchet USP 6,733,532 in view of Optimal Design of Synthetic Intervertebral Disc Prosthesis Considering Nonlinear Mechanical Behavior, Kweon et al., Dec. 20, 2001).
Spinal Kinetics, Inc.'s Second Amended Preliminary Invalidity Contentions—Exhibit 25 (chart comparing claims of USP 7,429,270 to Gauchet USP 6,733,532 in view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 26 (chart comparing claims of USP 7,429,270 to Baumgartner USP 5,370,697 in view of Stubstad USP 3,867,728).
Spinal Kinetics, Inc.'s Second Amended Preliminary Invalidity Contentions—Exhibit 27 (chart comparing claims of USP 7,429,270 to Coppes USP 7,563,284 in view of Stubstad USP 3,867,728).
Spinal Kinetics, Inc.'s Second Amended Preliminary Invalidity Contentions—Exhibit 28 (chart comparing claims of USP 7,429,270 to Baumgartner USP 5,370,697 in view of Stubstad Usp 3,867,728 in further view of Development and Characterization of a Prosthetic Intervertebral Disc, Hudgins, Georgia Inst. of Tech., Nov. 1998).
Spinal Kinetics, Inc.'s Second Amended Preliminary Invalidity Contentions—Exhibit 29 (chart comparing claims of USP 7,429,270 to Coppes USP 7,563,284 in view of Stubstad USP 3,867,728 further in view of Development and Characterization of a Prosthetic Intervertebral Disc, Hudgins, Georgia Inst. of Tech., Nov. 1998).
Burri et al., Neuentwicklung eines Implantates für den totalen Bandschiebenersatz, Vorgelegt von: Im Rahmen des Studiums für "Maschinenbau and Vergahrenstechnik" an der Eidgenöossischen Technischen Hochschule Zurich, im Feb. 2002).
English Translation of Burri et al., Neuentwicklung eines Implantates für den totalen Bandschiebenersatz, Vorgelegt von: Im Rahmen des Studiums für "Maschinenbau und Vergahrenstechnik" an der Eidgenöossischen Technischen Hochschule Zürich, im Feb. 2002), entitled Mechanical Engineering and Process Engineering at the Swiss Fedearl Institute of Technology Zurich (ETH Zurich) Feb. 2002.

(56) References Cited

OTHER PUBLICATIONS

Burri et al., Neuentwicklung eines lumbalen bewegungserhaltenden Bandscheibenimplantates, Feb. 25, 2002.
English Translation of Burri et al., Neuentwicklung eines lumbalen bewegungserhaltenden Bandscheibenimplantates, Feb. 25, 2002.
Hudgins, Development and Characterization of a Prosthetic Intervertebral Disc, Hudgins, Georgia Inst. of Tech., Nov. 1998.
Kweon et al., Optimal Design of Synthetic Intervertebral Disc Prosthesis Considering Nonlinear Mechanical Behavior, Dec. 20, 2001.

* cited by examiner

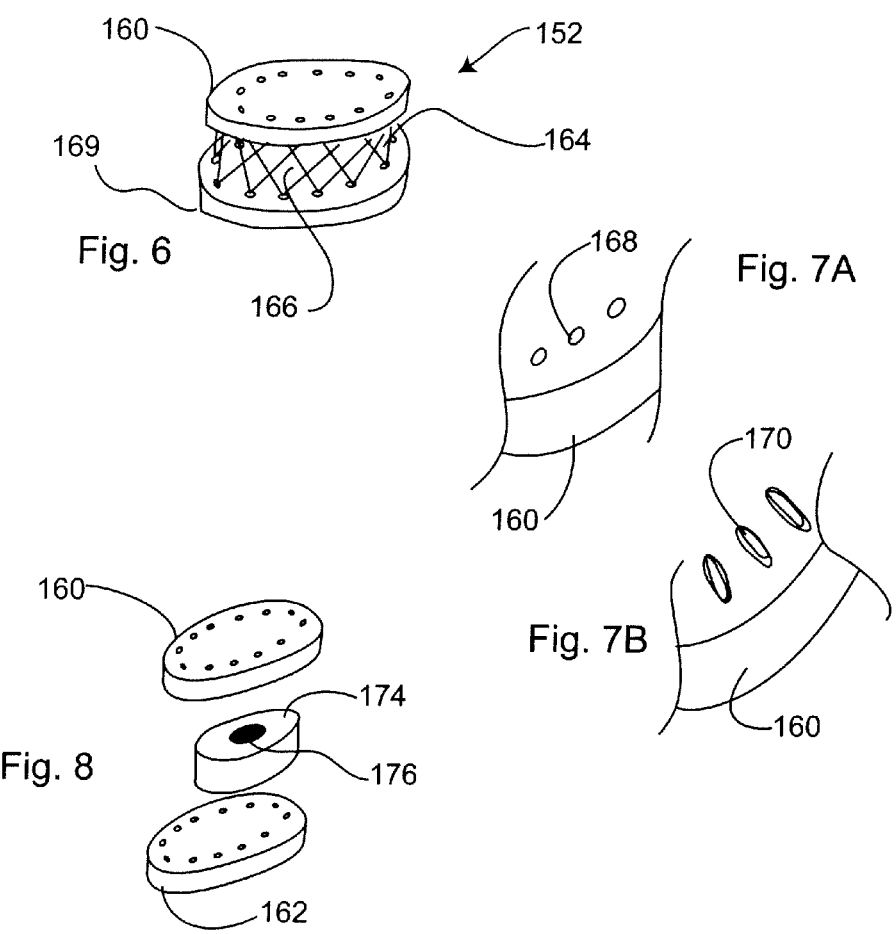

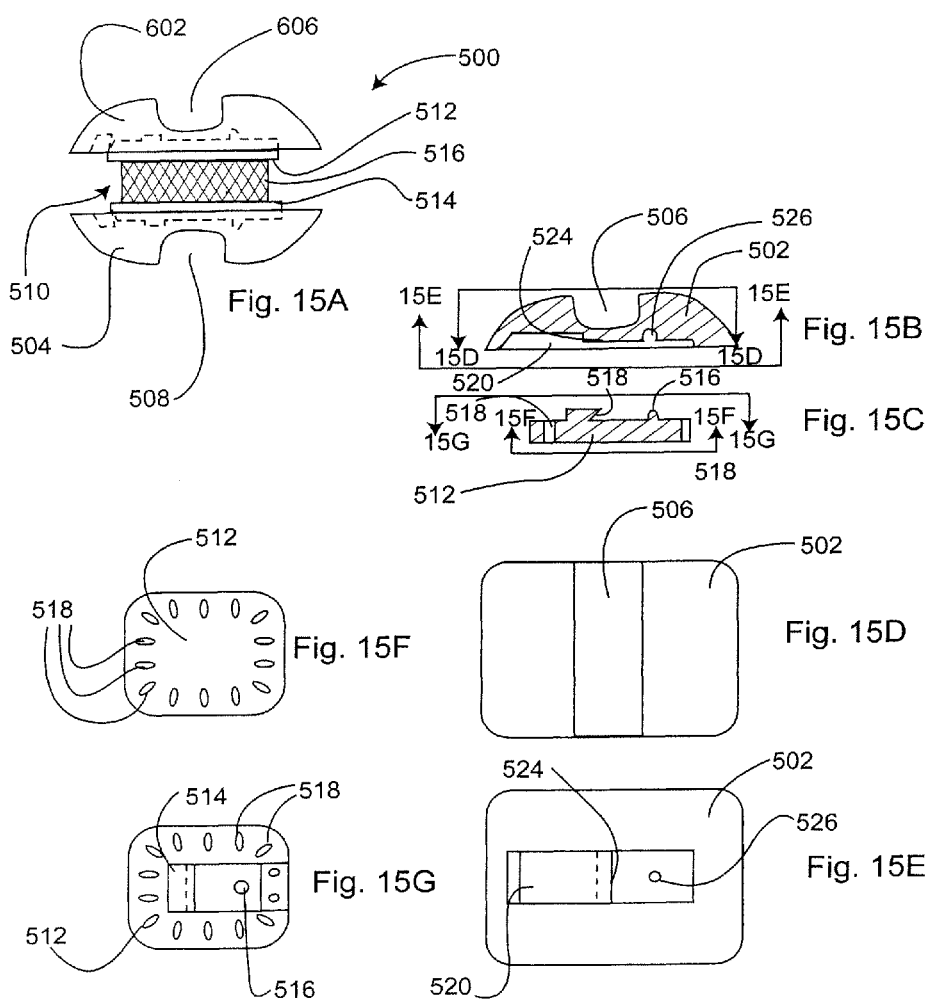

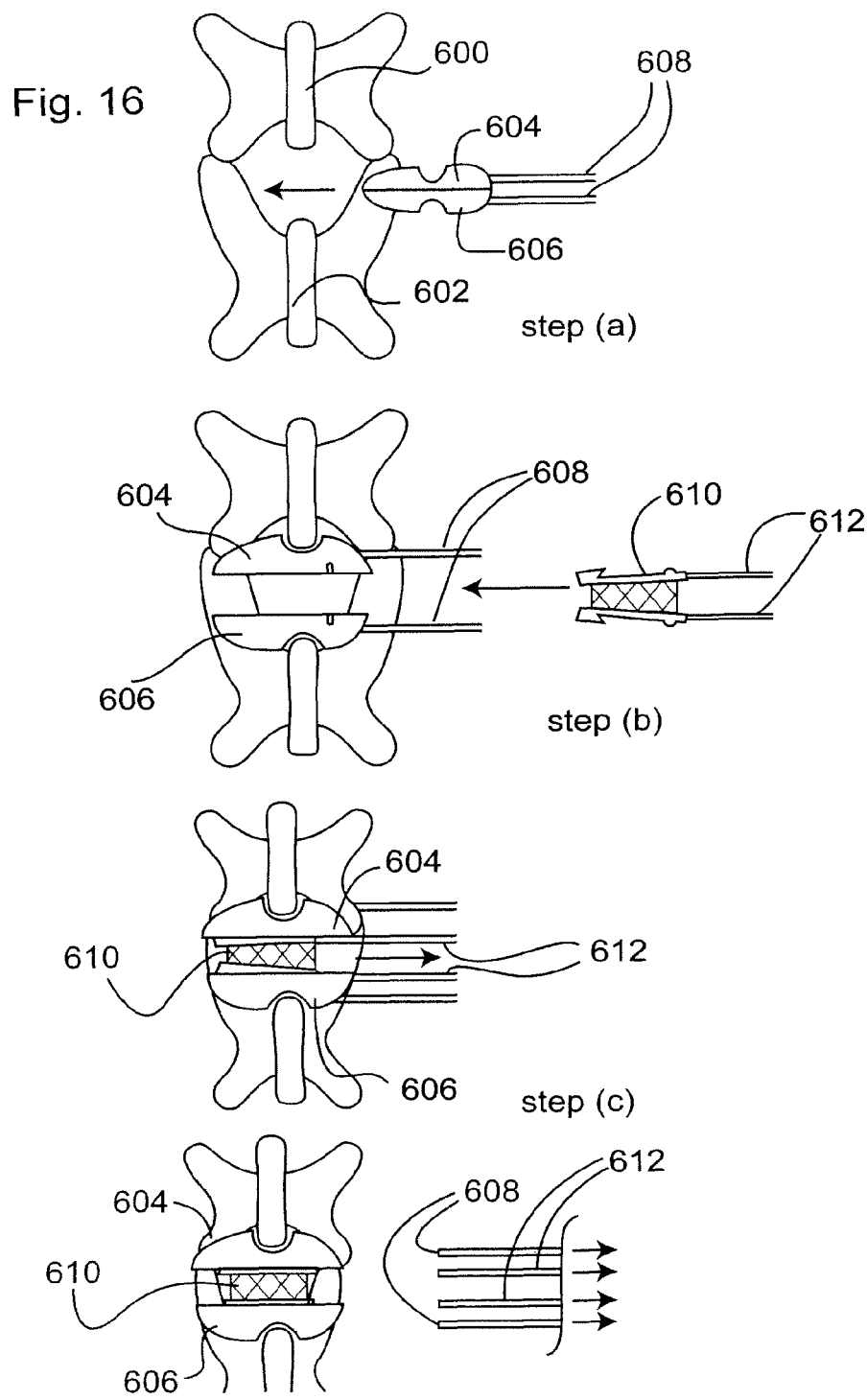

Fig. 17
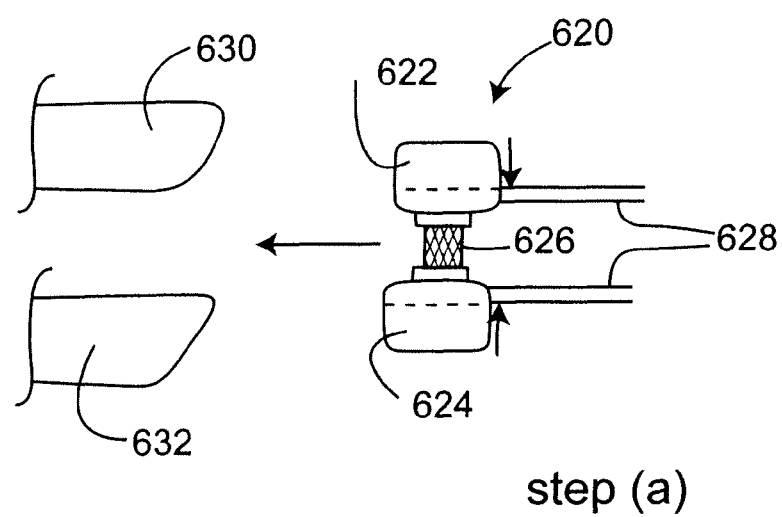
step (a)
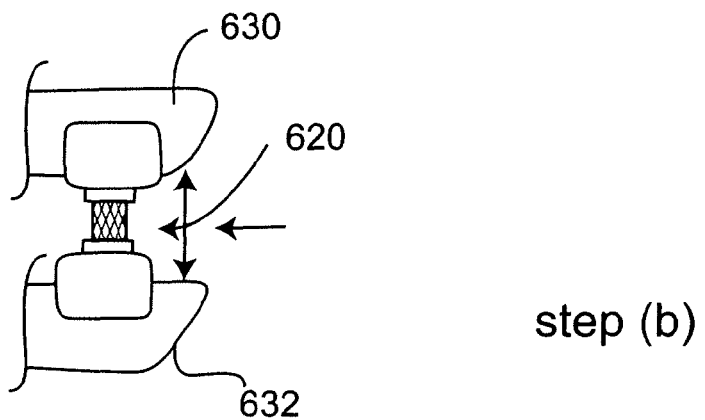
step (b)

INTER SPINOUS PROCESS SPACER WITH COMPRESSIBLE CORE PROVIDING DYNAMIC STABILIZATION

FIELD

The described devices are useful in the treatment of spinal disorders and pain. In particular, the described devices are designed to stabilize a portion of the spine by restoring and maintaining spacing between two adjacent vertebrae. The devices are compressible spacers that may be situated between the spinous processes of those adjacent vertebrae. The described inter spinous process spacers also allow a range of spinal motion and allow the joint to mimic the motion of a normally functioning spine.

BACKGROUND

There are a variety of spinal disorders that produce debilitating pain and affect a spinal segment's ability to properly function. The specific location or source of spinal pain is often an affected intervertebral disc or facet joint. A malady in one region of the spine may lead to deterioration and pain in another section of the spine One common approach to dealing with spinal pain, particularly pain associated with one or more affected intervertebral discs, is spinal fusion or arthrodesis. Spinal fusion is a procedure in which two or more adjacent vertebral bodies are fused together. Although spinal fusion is often effective in eliminating certain types of pain, the procedure has some detrimental effects. The procedure decreases spinal function by limiting the range of motion for the affected joint. Motion is decreased variously in flexion-extension, rotation, and side-to-side bending. The procedure increases the stress on each of the adjacent non-fused motion segments. It accelerates degeneration of those adjacent motion segments.

Prosthetic implantable intervertebral discs are a newer alternative for treating spinal pain. Some prosthetic discs, such as those produced by Spinal Kinetics Inc., Sunnyvale, Calif., preserve the natural biomechanics of the spine by recreating the full range of motion normally allowed by the elastic properties of the natural disc. Other implantable discs accomplish but a limited number of the properties and movement of the natural disc.

Other sources of spinal pain include the facet joints. They may be deformed, arthritic, injured, etc. Such disorders may lead to spinal stenosis, degenerative spondylolisthesis, and isthmic spondylolisthesis, and pinching of the nerves that extend between the affected vertebrae. Current treatments include removal of the facet joints (facetectomy). Such treatment may provide pain relief, but since the facet joints help to support various loads on the spinal column in addition to providing a sliding articulation and mechanism for load transmission, their removal corrupts natural spinal movement. Laminectomy (removal of the lamina, including the spinal arch and the spinous process) may also provide pain relief associated with facet joint disorders; however, the spine is made less stable by such removal.

Various attempts have been made at facet joint replacement. Many such replacements are inadequate since the involved prosthetic facet joints preserve existing bony structures but do not address pathologies that affect the facet joints themselves. Certain facet joint prostheses, such as disclosed in U.S. Pat. No. 6,132,464, are intended to be supported on the lamina or the posterior arch. Since the lamina are very complex and highly variable anatomical structures, it is very difficult to design a prosthesis that provides reproducible positioning against the lamina and to correctly locate the prosthetic facet joints. Prosthetic facet joints such as disclosed in U.S. Pat. No. 6,579,319, require replacement of the natural facet joint and are unlikely to endure the loads and cycling experienced by the vertebra. Such prosthetic facet joints may shift over time. Further, such prosthetic joints do not treat disease or trauma to other structures of a vertebra, such as the lamina, spinous process, or transverse processes.

Dynamic posterior stabilization surgical procedures address spinal pain resulting from more than one disorder, specifically when more than one structure of the spine has been compromised. Many such procedures and structures are intended to provide support to fusion-based implants while maximizing the natural biomechanics of the spine. Such dynamic posterior stabilization systems typically fall into one of two general categories: posterior pedicle screw-based systems and inter spinous process spacers.

Examples of pedicle screw-based systems may be found in U.S. Pat. Nos. 5,015,247, 5,484,437, 5,489,308, 5,609,636, 5,658,337, 5,741,253, 6,080,155, 6,096,038, 6,264,656 and 6,270,498. These types of systems involve the use of screws that are positioned in the vertebral body through pedicles. Certain of these pedicle screw-based systems may be used to augment compromised facet joints, while others require removal of the spinous process or the facet joints for implantation. One such system, the Zimmer Spine Dynesys. employs a cord that is extended between the pedicle screws and a fairly rigid spacer which is passed over the cord and positioned between the screws. Although this system is able to provide load sharing and restoration of disc height, because it is so rigid, it is not effective in preserving the natural motion of the spinal segment into which it is implanted. Other pedicle screw-based systems employ articulating joints between the pedicle screws. Because these types of systems require pedicle screws, implantation of the systems are often more invasive to implant than inter spinous process spacers.

Where the level of disability or pain to the affected spinal motion segments is modest or where the condition, such as an injury, is not chronic, the use of inter spinous process spacers is preferred over pedicle based systems since they require a less invasive implantation approach and less dissection of the surrounding tissue and ligaments. Examples of inter spinous process spacers are disclosed in U.S. Pat. Nos. Re. 36,211, 5,645,599, 6,149,642, 6,500,178, 6,695,842, 6,716,245, and 6,761,720. The spacers are placed between adjacent spinous processes. Spacers produced from harder materials are fixed in place by opposing or squeezing forces on the spacer imposed by the distraction of the affected spinal segments or by use of keels or screws that anchor into the spinous process. Although implanting hard or solid inter spinous process spacers is less invasive than implanting a pedicle screw-based dynamic stabilization system, such procedures still require dissection of muscle tissue and of various spinous ligaments. Additionally, these harder devices promote spinal motion that is less analogous to the natural spinal motion than are the more compliant and flexible inter spinous process spacers. Additionally, delivery of compliant or flexible inter spinous process spacers is less invasive than is the delivery of those that are not compliant or flexible. However, their compliancy makes them more susceptible to displacement or migration over time. To lessen this risk, many such spacers employ straps wrapped around the adjacent spinous processes to situate the spacers. Of course, these straps require dissection of additional tissue and ligament within the adjacent inter spinous process spaces.

None of the cited patents show the structures and procedures described herein.

SUMMARY

We describe an inter spinous process spacer device that provides dynamic stabilization to regions of the spine. The device may be placed between adjacent (or, first and second) spinous processes forming portions of adjacent vertebral bodies. The vertebral bodies have both facet joints and foramenal spaces. The device may be made up of at least one central core assembly, in turn made up of first and second end plates and at least one compressible core member positioned between those end plates.

The core member itself is made of at least one compressible core member, perhaps of one or more physiologically acceptable polymers, e.g., elastomeric materials, such as polysiloxane, polyurethane, polyurethane-polycarbonate elastomers, poly(ethylene propylene) copolymer, polyvinylchloride, poly(tetrafluoro ethylene) and copolymers, hydrogels, and the like.

The at least one fiber often extends between and engages the end plates. Attached to the end plates, and attachable to the spinous processes, are bone attachment members or connectors.

The at least one central core assembly is configured to stabilize the spacing between the first and second spinous processes, to provide for compression, to permit rotation, and to permit lateral bending, specifically, to provide shock absorbing, and to permit axial rotation, motion in flexion-extension, and motion from side-to-side. Overall, the size of the device may be chosen so that, when implanted, it restores the posterior tension band, realigns the facets associated with the two vertebral bodies, and restores the foramenal heights associated with those vertebral bodies.

The device may be configured to be implanted by a posterior or lateral approach.

In one variation, the device may include bone attachment members that are configured for attachment to the end plates in situ after the bone attachment members are attached to the spinous processes.

In another variation, the device may include bone attachment members configured to be attached to the end plates in situ by a one-sided or two-sided lateral approach or a posterior approach to the spinous processes, after the bone attachment members are attached to the spinous processes.

The end plates each have a periphery and the at least one fiber extending between the end plates may be wound around the periphery of each of the end plates.

The devices may have one or more central core core assemblies perhaps positioned to be substantially parallel to a vertical axis of the spinous processes or positioned not to be substantially parallel to the vertical axis of the spinous processes.

The devices may have end plates with interior surfaces, i.e., the surfaces adjacent to the compressible core member, that are substantially flat, curved, or include a bearing component configured to allow limited relative movement between the end plates.

The devices may include bone attachment members or bone fixation elements or bone connectors such as keels or spikes.

The fibers may be wrapped from and attach one end plate to the other end plate perhaps through openings in the end plates or wherein the fibers are in the form of a jacket fixedly attached to the end plates. The jacket may be made of woven or unwoven fabric.

In some variations, the device may have multiple bone connectors on a single end plate, configured to attach to one or two compressible core members fixedly attached both to the other end plate.

BRIEF DESCRIPTION OF THE DRAWINGS

FIG. 6 is a perspective view of the core component of our spacer.

FIGS. 7A and 7B show, respectively, partial, cutaway, perspective views of edges of the top and bottom endplate components of our spacer.

FIG. 8 shows a blown-up, perspective view of the core with the fiber layer or layers omitted for clarity.

FIGS. 15A-15G show an inter spinous process spacer variation that is assembled during implantation and is introduced laterally into the inter spinous process space.

FIG. 16 shows a process for implanting the device shown in FIGS. 15A-15G.

FIG. 17 provides a schematic procedure for implanting a version of our dynamic spacer by a posterior approach.

DESCRIPTION

Figure 1:
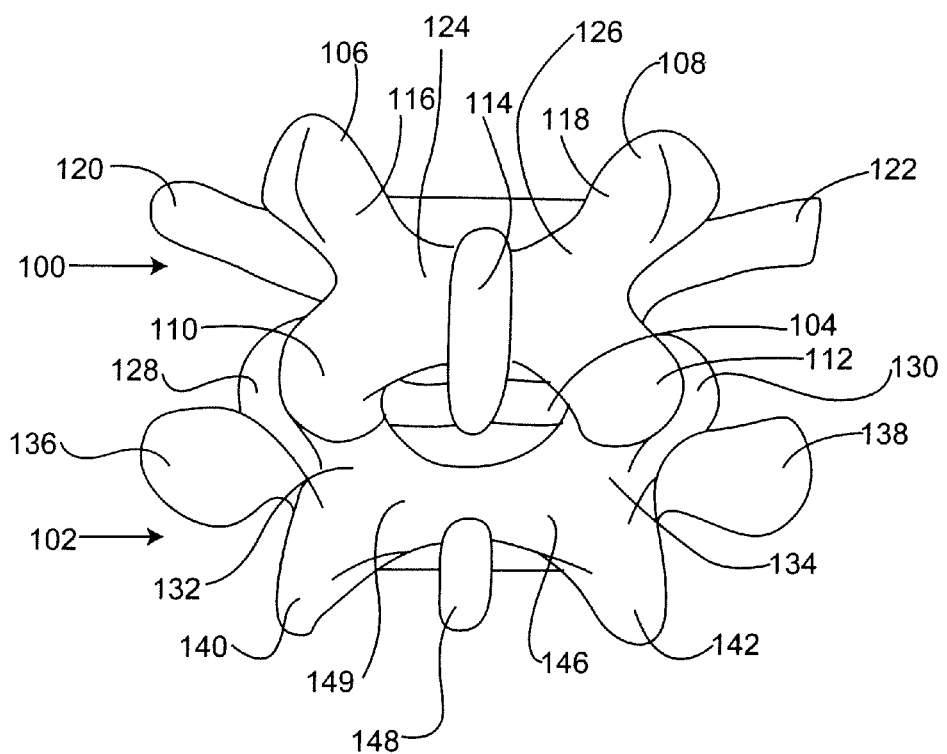
FIGS. 1-4 show the anatomy of a spinal unit and certain conventions in describing vertebral movement.

FIG. 1 shows a portion of the human spine having an upper or superior vertebra (100) and an inferior or lower vertebra (102). An intervertebral disc (104) is located in between the two vertebrae (100, 102). The upper vertebra (100) has superior facet joints (106) and (108), inferior facet joints (110) and (112), and upper spinous process (114). Pedicles (116) and (118) interconnect the superior facet joints (106) and (108) to the upper vertebra (100). Transverse processes (120) and (122) extend laterally from the superior facet joints (106) and (108), respectively. Extending between each of the inferior facet joints (110) and (112) and the upper spinous process (114) are laminal zones (124) and (126), respectively.

The lower vertebra (102) has superior facet joints (128) and (130), superior pedicles (132) and (134), transverse processes (136) and (138), inferior facet joints (140) and (142), laminal zones (144) and (146), and lower spinous process (148).

The upper vertebra with its inferior facets, the lower vertebra with its superior facet joints, the intervertebral disc, and the associated spinal ligaments extending between the vertebrae together make up a spinal motion segment or functional spine unit. Collectively, the facet joints, laminas and spinal processes are the "posterior element" of a spinal motion segment. Each such spinal motion segment allows that portion of the spine to move along three orthogonal axes, both in rotation and in translation. Those various spinal motions are illustrated in FIGS. 2-4.

Figure 2:
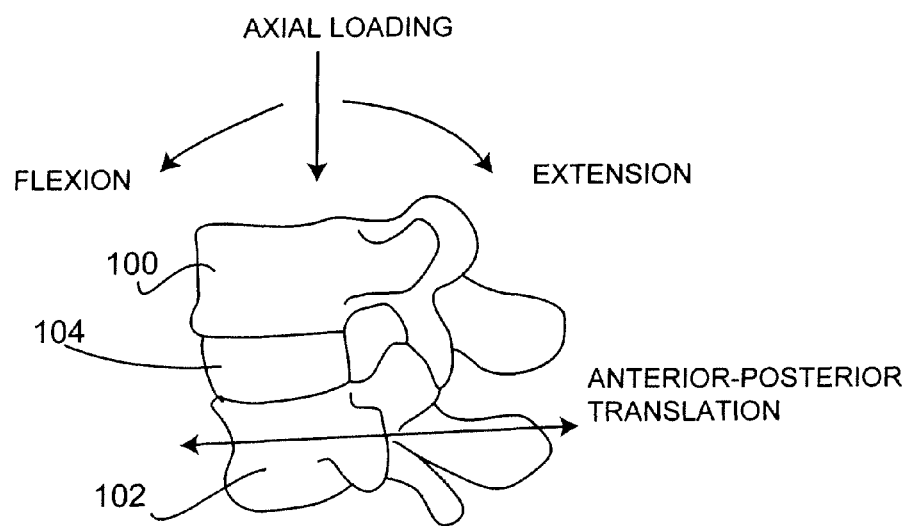

In particular, FIG. 2 provides a side view of the spinal motion segment. The Figure shows flexion and extension motions, which are essentially rotational motions of the upper vertebra (100) with respect to the lower vertebra (102), and axial loading of the functional spine unit. The Figure also shows anterior-posterior translation (e.g., linear motion of the lower vertebra (102) with respect to upper vertebra (100)).

Figure 3:
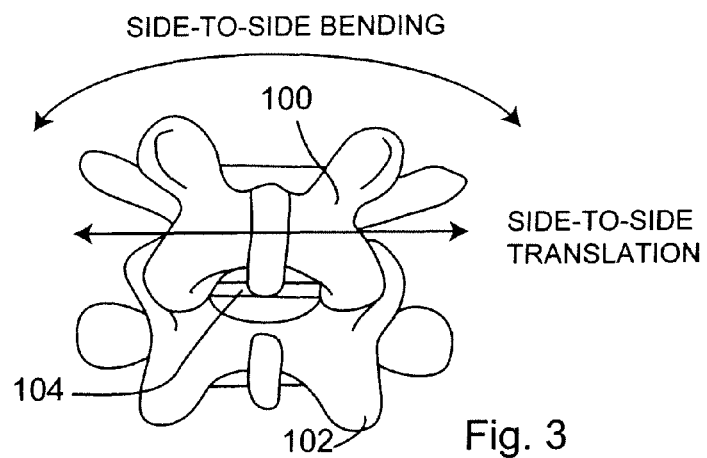

FIG. 3 provides a rear view of the spinal motion segment and shows lateral bending motions and linear side-to-side movement or translation of one vertebra (102) with respect to the other (100).

Figure 4:
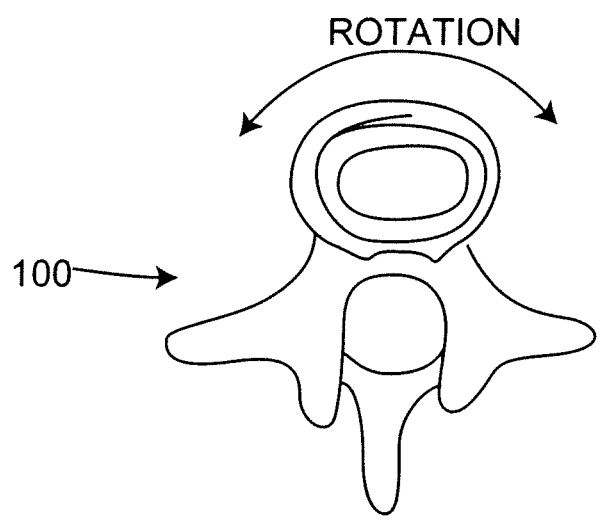

FIG. 4 provides a top view of the spinal motion segment and depicts shows axial rotational motion. A normally functioning spinal motion segment provides rotational resistance and angular limits to that rotation in each illustrated direction.

Pain in the lower extremities is often caused by the compression of spinal nerve roots by a bulging disc. Lower back pain is often caused by collapse of the disc and by the adverse effects of articulation weight through a damaged, unstable vertebral joint. In some cases, when a patient having a collapsed disc moves in extension (e.g., leans backward), the posterior portion of the annulus fibrosus may further compress and extend into the spinal canal. This condition (called "spinal stenosis") produces a narrowing of the spinal canal and impingement of tissue upon the spinal cord, thereby producing pain.

Our devices and methods reduce or eliminate back pain while maintaining near normal anatomical motion. Specifically, these dynamic spacers may be used to provide dynamic bias and spacing. They may be used individually or in combination, to eliminate nerve impingement associated with a damaged disc and to reinforce a damaged disc, while permitting relative movement of the vertebrae adjacent the damaged disc.

Our dynamic spacers are particularly well suited for minimally invasive methods of implantation.

Our dynamic spacers may be used apply a bias force to vertebrae adjacent to (i.e., on either side of) a damaged disc, while permitting relative movement of the vertebrae. By applying a bias force disc height may be restored, thereby reducing nerve impingement. By restoring disc height, our dynamic spacers retract disc protrusions into the normal disc space thereby reducing nerve impingement by the protrusions; reduce the load carried by the facet joints lowering nerve impingement originating at those joints; restore intervertebral spacing also lowering nerve impingement by the intervertebral foramina; and reduce pressure on portions of the annulus thereby alleviating nerve impingement in disc fissures.

Our dynamic spacers may be used to reinforce a damaged disc, restore disc height, or bear some or all of the load normally carried by a healthy disc. Some variations of our device may, particularly when used in multiples, have integral or independent portions that are relatively stiff, and thus serve to reinforce or to functionally support the disc. Other variations having larger footprints that also are stiff, also serve to reinforce or to functionally support the disc. By doing so, disc protrusions may reduced or prevented, thereby eliminating nerve impingement by the protrusions. By bearing some of the load normally carried by a healthy disc, the load may be redistributed as needed, such as when a dynamic bias device is used.

Figure 5B:
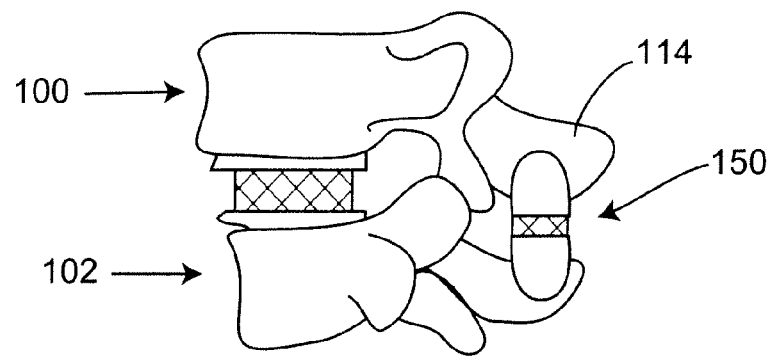
FIGS. 5A and 5B show implantation and placement of our spacers on spinous processes with and without prosthetic discs.
Figure 5A:
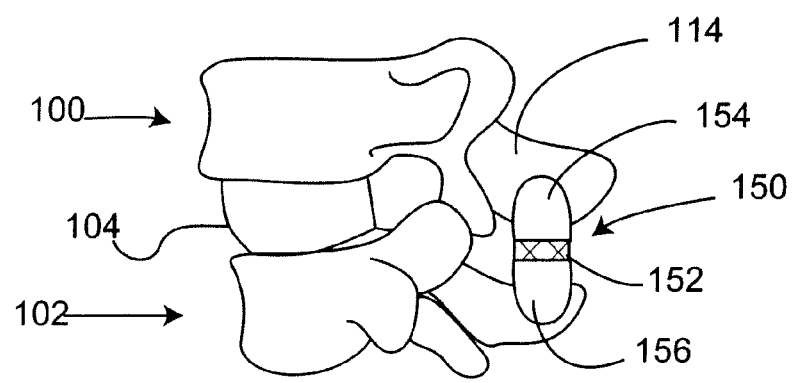

FIGS. 5A and 5B provide side view, generic representations of the placement of our inter spinous process spacers (150) and illustrate certain conventions in our nomenclature. In general, our spacers comprise a central section (152) comprising one or more compressible cores of the structure described below and upper (154) and lower (156) inter spinous process attachments. The core in the central section (152) absorbs shock and is compressible. The upper (154) and lower (156) inter spinous process attachments are to affix the device to the respective spinous processes.

In FIG. 5A, the device (150) is situated between the upper (114) and lower (148) inter spinous processes. They may be implanted in positions more anterior or more posterior than the positions shown in FIGS. 5A and 5B depending upon the design of a particular device and its intended use, e.g., purely a spacer or as a source of bias between the adjacent vertebrae. In any case, as mentioned elsewhere, our devices may be used between two adjacent spinous processes with or without placement of complementary implants, e.g., a disc implant, in the spinal motion segment. FIG. 5A shows the placement of our device (150) in a spinal motion segment having a natural disc (104).

FIG. 5B shows the placement of our device (150) in a spinal motion segment having an implanted artificial disc (104).

Again, our inter spinous process spacers (150) comprise a central section (152) comprising one or more compressible cores of the structure described below and upper (154) and lower (156) inter spinous process attachments or end plates.

FIG. 6 depicts an isolated core (152). The core (152) further comprises both an upper (or top) (160) and lower (or bottom) endplate (162), where the upper and lower endplates are separated from each other by a compressible element (164). In the core structure, the top (160) and bottom endplates (162) are held together by at least one fiber (166) wound around at least one portion of each of the top (160) and bottom endplates (162). As such, the two endplates (or planar substrates) are joined to each other by one or more fibers (166) that are wrapped around at least one portion of the top (160) and bottom endplates (162).

The core (152) with its upper (160) and lower endplates (162) may be integrated into the adjacent upper and lower spinous process spacer attachments or one or both of the endplates may be configured to be attachable to those spinous process spacer attachments.

FIGS. 7A and 7B show, respectively, partial, cutaway, perspective views of edges of the top (160) and bottom endplates (162). In particular, FIG. 7A shows openings (168) in the endplate (160) that are generally round, through which the noted fibers (e.g., (166) in FIG. 6)) may be wound. Similarly, FIG. 7B shows openings (170) in the endplate (160) that are generally slotted.

The top (160) and bottom endplates (162) may be fabricated from a physiologically acceptable material that provides for the requisite mechanical properties, e.g., titanium, titanium alloys, stainless steel, cobalt/chromium, etc.; plastics such as polyethylene with ultra high molar mass (molecular weight) (UHMW-PE), polyether ether ketone (PEEK), etc.; ceramics; graphite; etc.

The fibrous elements may be made up of one or more fibers, where the fibers are generally high tenacity fibers with a high modulus of elasticity. The fibers may have a high modulus of elasticity, e.g., at least about 50 MPa, and a diameter that ranges from about 0.25 mm to about 8 mm. The fibers making up the fibrous compressible elements may be fabricated from a suitable material, e.g., polyester (e.g., Dacron), polyethylene, polyaramid, carbon or glass fibers, polyethylene terephthalate, acrylic polymers, methacrylic polymers, polyurethane, polyurea, polyolefin, halogenated polyolefin, polysaccharide, vinylic polymer, polyphosphazene, polysiloxane, and the like.

The fibers wound around one or more regions of the top or bottom plates may make up a variety of different configurations. For example, the fibers may be wound in a pattern that has an oblique orientation. The number of layers of fiber winding may be varied to achieve suitable mechanical properties.

The fibers are typically limited to the annular region of the core. They may include both oblique and horizontal windings. A separate polymeric component comprises the nucleus of one variation of the core. The tension placed on the fibers of each layer may be the same or varied.

FIG. 8 shows a blown-up, perspective view of the core with the fiber layer or layers omitted for clarity. The core (152) may further include an annular region (176) that forms the periphery of the core and a nuclear region (178) in the center of the disc and surrounded by the annulus (176).

The core (152) may comprise one or more polymeric components. The polymeric component may be fabricated from a variety of physiologically acceptable polymers, e.g., elastomeric materials, such as polysiloxane, polyurethane, polyurethane-polycarbonate elastomers, poly(ethylene propylene) copolymer, polyvinylchloride, poly(tetrafluoro ethylene) and copolymers, hydrogels, and the like.

The polymeric component may be limited to particular regions, e.g., the annular (176) or nucleus (178) regions. In some variations, the polymeric component is limited to the nuclear region of the core. In other variations, both the annular and nuclear regions are polymeric. Depending upon the desired configuration and mechanical properties, the polymeric component may be integrated with the fibrous component, such that at least a portion of the fibers of the fibrous component is embedded in, e.g., complexed with, at least a portion of the polymeric component. In other words, at least a portion of the fibrous component is impregnated with at least a portion of the polymeric component.

The core may include one or more different polymeric components. In those variations where two or more different polymeric components are present, any two given polymeric components are considered different if they differ from each other in terms of at least one aspect, e.g., composition, cross-linking density, and the like. As such, the two or more different polymeric components may be fabricated from the same polymeric molecules, but differ from each other in terms of one or more of: cross-linking density; fillers; etc. For example, the same polymeric material may be present in both the annulus and nucleus of the disc, but the crosslink density of the annulus polymeric component may be higher than that of the nuclear region. In yet other variations, polymeric materials that differ from each other with respect to the polymeric molecules from which they are made may be employed.

By selecting particular fibrous component and polymeric component materials and configurations, e.g., from the different representative formats described above, a core with desired characteristics may be produced.

Representative particular combinations of interest include:
1. Biocompatible polyurethane, such as Ethicon Biomer, reinforced with Dacron poly(ethylene terephthalate) fiber, or Spectra polyethylene fiber, or Kevlar polyaramide fiber, or carbon fiber.
2. Biocompatible polysiloxane modified styrene-ethylene butylene block copolymer sold under C-Flex tradename reinforced with Dacron poly(ethylene terephthalate) fiber, or Spectra polyethylene fiber, or Kevlar polyaramide fiber, or carbon fiber.
3. Biocompatible Silastic silicone rubber, reinforced with Dacron poly(ethylene terephthalate) fiber, or Spectra polyethylene fiber, or Kevlar polyaramide fiber, or carbon fiber.

Our inter spinous process dynamic spacer device restores disc height and, by conservation of disc volume, retracts the protrusion into the normal disc space thereby reducing nerve impingement by the protrusion. Restoring disc height also reduces the load carried by the facet joints thereby eliminating nerve impingement originating at the joint, restores intervertebral spacing thereby eliminating nerve impingement by the inter-vertebral foramina, and reduces pressure on portions of the annulus thereby alleviating nerve impingement in disc fissures.

Returning to FIGS. 5A and 5B, our inter spinous process dynamic spacer device may apply a bias force to the adjacent vertebrae (100) and (102) to which it is connected, but allow relative movement between vertebrae (100) and (102).

Our inter spinous process dynamic spacer device may apply a bias force between the vertebrae (100) and (102) that tends to push the two vertebrae apart when the disc height is normal or less than normal. The bias force is preferably selected such that the disc height is normal with normal posture and loading, and increases with posterior flexure or added axial compressive load. Anterior-posterior biases and lateral biases between vertebrae (100) and (102) may also be applied as desired.

Since most protrusions are located in a more posterior region of the disc, locating our device comparatively more posterior on the spinous processes tends to shift the load carried by the disc from the posterior portion of the disc towards the anterior portion of the disc. Such a location also tends to reduce the load carried by the facet joints.

Said another way, our device may be used to provide a substantially vertical, or axial, bias force, with the direction independent of displacement.

As mentioned above, one or more of our inter spinous process dynamic spacer devices (150) may be implanted, either alone or in combination. When used in combinations of two to treat posterior protrusions, facet joint degradation, and nerve impingement by intervertebral foraminae, our spacer devices may be designed such that the physical parameters of the two devices are different, e.g., the more anterior device may be stiffer and the more posterior device may be selected to provide an attractive bias thereby creating a "lever" effect using the anterior device as a fulcrum and the two spinous processes as levers.

Figure 9:
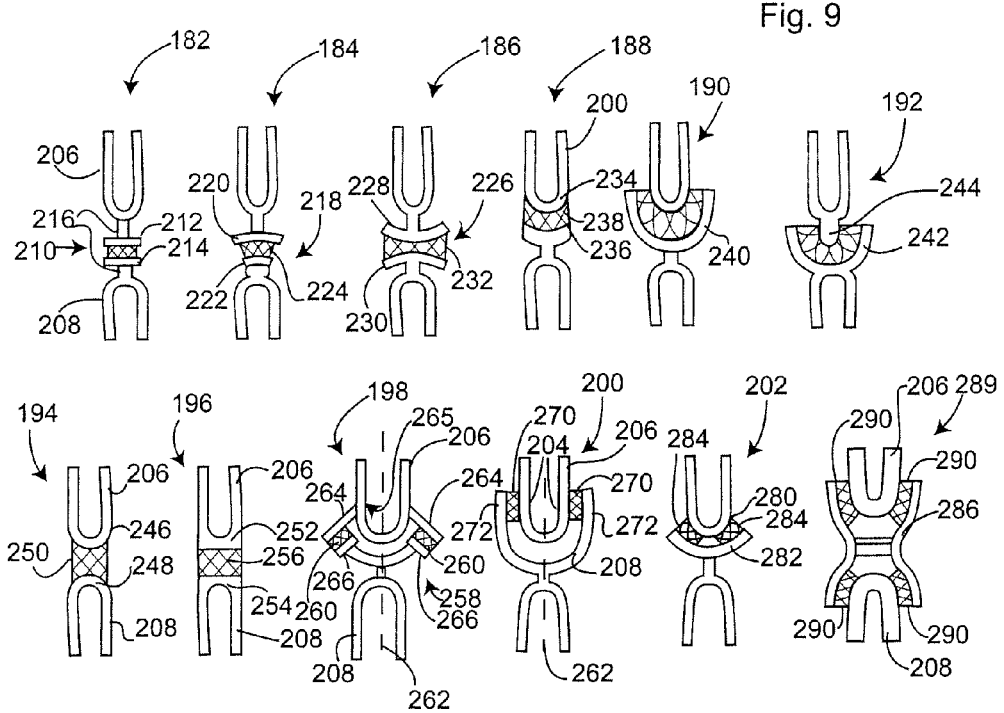
FIG. 9 shows front views of several variations of our dynamic inter spinous process spacer.

FIG. 9 shows front views of several variations of our dynamic inter spinous process spacer. Each variation shown in FIG. 9 includes an upper spinous process attachment member (206) and a lower attachment member (208). Examples of suitable integrated and non-integrated attachment members are discussed below. The first variation (182) includes a core (210) further comprising upper (212) and lower (214) end plates. The end plates are generally planar and are connected to the attachment members by pillars (216).

Variation (184) includes a core (218) having upper (220) and lower (222) end plates having generally semicircular cross-sections and form portions of cylinders. The cylinders nestle within each other separated by the compliant core member (224).

Variation (186) also includes a core (226) having semi-cylindrical end plates (228, 230) but in this variation, the outer surfaces of the semi cylinders face each other and are adjacent the compliant core member (232).

Variation (188) is a spacer where the upper end plate (234) is integrated with the upper attachment member (206). The lower end plate (236) is semi cylindrical in shape and includes an inner surface that is generally parallel to the outer surface of the upper end plate (234) but separated by the compliant core member (238).

Variation (190) is similar to variation (188) but the lower end plate (240) is hemi-cylindrical in shape.

Variation (192) includes a hemi cylindrical lower end plate (242) and a quite narrow upper end plate (244).

Variation (194) includes upper (246) and lower (248) end plates that are integrated into the upper (206) and lower (208) attachment members separated by the compliant core member (250). The surfaces of the upper (246) and lower (248) end plates that are contiguous with the compliant core member (250) are curved.

Variation (196) also includes upper (252) and lower (254) end plates that are integrated into the upper (206) and lower (208) attachment members separated by the compliant core member (256). The surfaces of the upper (252) and lower (254) end plates that are contiguous with the compliant core member (250) are substantially planar.

Variation (198) comprises a core (258) having multiple compliant core members (260) situated laterally and at an angle to the center line (262) of the spacer (198). The upper end plates (264) laterally extend from the upper attachment member (206) at an angle (265) less than 90° to the center line (262). The lower end plates (266) are substantially parallel to the upper end plates (264) and separated from those upper end plates (264) by compliant core members (260).

Variation (200) also includes multiple compliant core members (270) where the end plates (272, 274) are integrated into the upper (206) and lower (208) attachment members and are parallel to the center line (262) of the spacer (200).

Variation (202) includes a curved upper end plate (280) and a curved lower end plate (282) separated by a pair of compliant core members (284).

Variation (204) includes a third member (286) contiguous to multiple compliant core members (290) where the compliant core members (290), in turn, are attached to upper (206) and lower attachment members.

Each of the variations shown in FIG. 9 has unique compression characteristics, lateral movement characteristics, and twisting characteristics. Limits on the movement of the spinous processes may be selected by choosing the size and configuration of the end plates in the device.

Although we have chosen "upper" and "lower" in describing the device here, each of the variations so-described may be "flipped" end-for-end and implanted in that position.

Figure 10:
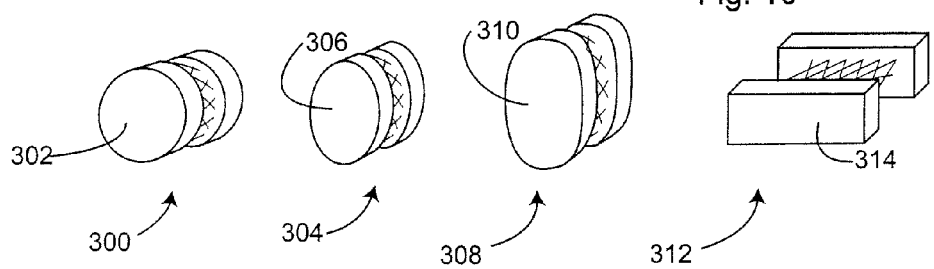
FIG. 10 shows examples of end plate shapes, and those of the associated compliant core members, that are acceptable in our device.

The shape of the end plates may be chosen to attain specific physical attributes. FIG. 10 shows examples of end plate shapes, and those of the associated compliant core members, that are acceptable in our device. Core (300) has a round end plate (302). Core (304) has oval end plates (306). Core (308) has elongated end plates (310) with a straight portion on the long sides. Core (312) has rectangular end plates (314).

Figure 11:
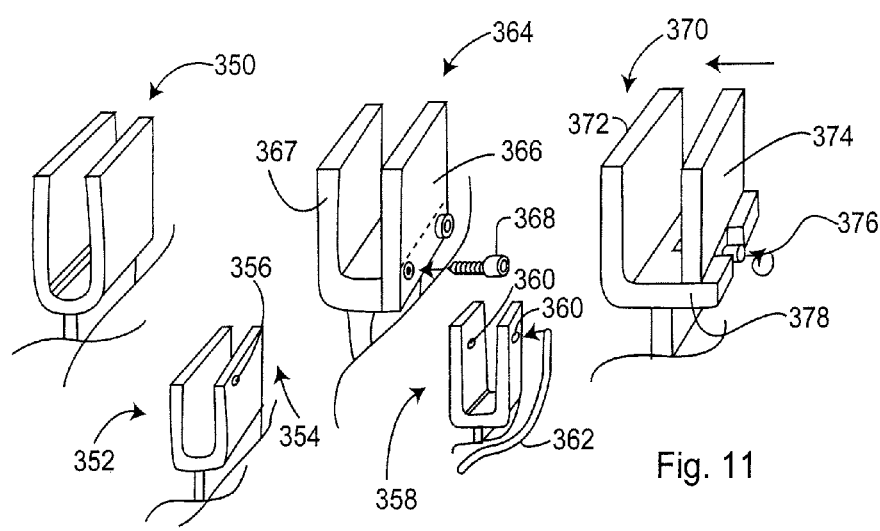
FIGS. 11 and 12 show a number of examples of spinous process attachment members suitable for use in our device.
Figure 12:
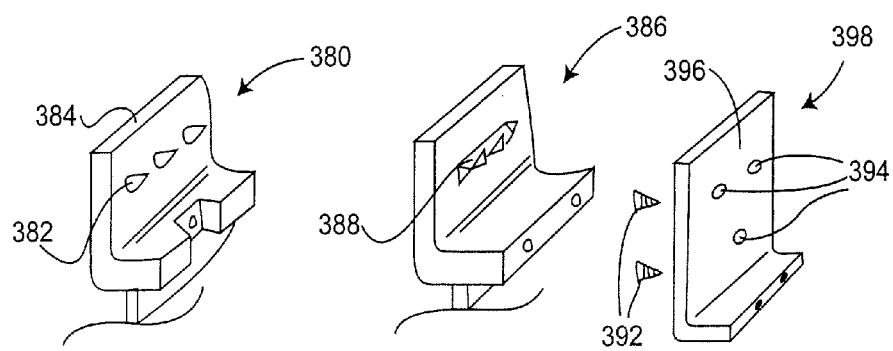

FIGS. 11 and 12 show a number of examples of spinous process attachment members suitable for use in our device.

In FIG. 11, a first variation (350) of the attachment member is a simple U-shaped that may be slipped onto the spinous process from the posterior. In some variations, the member (350) may be used without additional placement components or features in that, for instance, the spacer device may be used in tension to push (or bias) the adjacent spinous processes apart. The pressure imposed by the spine itself, in some such situations, is adequate to hold the member (350) in place.

Variation (352) is an attachment member similar to variation (350) but includes an attachment or stabilizing screw (354) that passes through an opening (356) in the wall of the attachment member (352). More than one opening (356) and the accompanying screw (354) may, of course, be used in an attachment member (352).

Another variation (358), also includes one or more openings (360) in the wall of the attachment member (358) with matching openings in the other wall. In this variation (358), the openings (360) accommodate one or more fibrous members (362) passing through similar openings formed in the body of the spinous member to which the attachment member (358) is attached.

Variation (364) is an attachment member having a removable (and attachable) wall (366) secured to the remainder of the member (364) by fasteners (368) such as screws. This allows the attachment member (364) to be introduced laterally to the space between the spinous processes.

Similarly, variation (370) is an attachment member that has an adjustable space between the fixed wall (372) and the movable wall (374). The size of the space is changed by using rotating screw (376) engaging a threaded opening in movable wall (374) and rotatably fixed in the base (378) of the attachment member (370).

FIG. 12 shows a number of attachment member components having fixation elements for affixing the attachment member to the spinous process. These fixation elements, as should be apparent, assist the inter spinous process spacer in providing effective limits to the separation of the two spinous processes during flexion of the spine and otherwise provides secure positioning of the spacer after implantation.

Variation (380) includes a number of spikes (382) extending into the space into which the spinous process is to be placed. This example of an attachment member component (380) is similar to the variation (370) shown in FIG. 11. It includes a fixed wall (384). The fixed wall section (384) may be introduced laterally onto the spinous process and, as the movable wall (not shown) is tightened onto the spinous process, the spikes (382) engage the spinous process and fix the spacer assembly to the engaged spinous process. The movable wall may have spikes or the like as well.

Variation (386) is a fixed wall component similar to the fixed wall component (367) of variation (364) shown in FIG. 11. The fixation element in this variation comprises a barbed keel (388). The spinous process onto which this fixed wall component (386) is placed may, if the chosen size of the keel (388) is appropriate, be prepared by creating a groove in the spinous process into which the keel (388) fits. If the keel (388) is short, no such preparation would be needed.

Variation (390) is a fixed wall component using screws (392) that pass through openings (394) in the wall (396).

Figure 13:
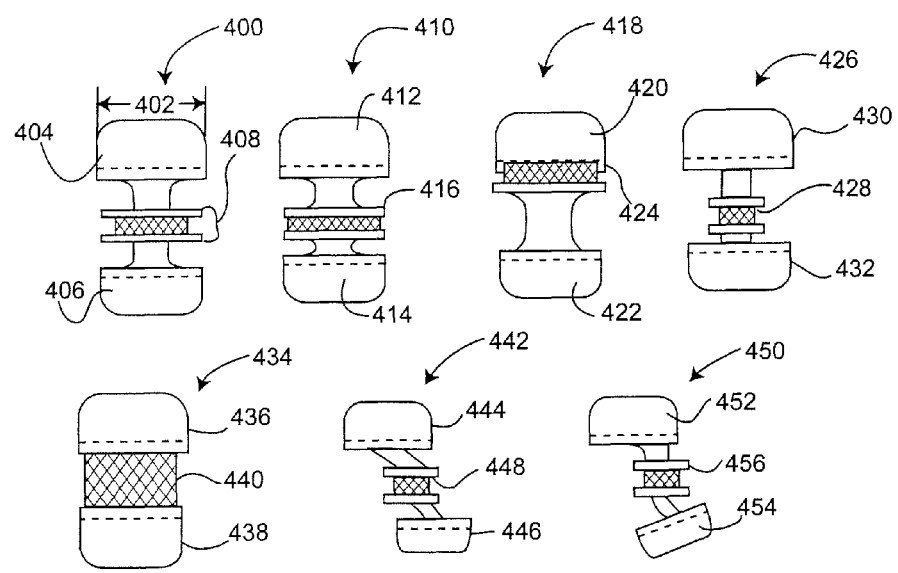
FIG. 13 provides side views of a number of our spinous process spacers showing examples of the positioning of the core assembly and the spinous process attachment members.

FIG. 13 provides side views of a number of our spinous process spacers showing examples the positioning of the core assembly and the spinous process attachment members.

Inter spinous process spacer (400) includes relatively long (402) upper (404) and lower (406) spinous process attachment members and a core assembly (408) that is not adjacent either attachment member (404, 406).

Inter spinous process spacer (410) also includes relatively long upper (412) and lower (414) spinous process attachment members but, in this instance, the core assembly (416) is not adjacent either of the attachment members (404, 406) nor is the core equidistant from the attachment members (404, 406). The core assembly (416) is located closer to the lower spinous attachment member (414).

Inter spinous process spacer variation (418) also includes relatively long upper (420) and lower (422) spinous process attachment members. The core assembly (424) is adjacent upper attachment member (420). The core assembly may be situated adjacent to lower attachment member (422).

The core assemblies in inter spinous process spacers (400, 410, 418) also have relatively long fore-aft dimensions, i.e., along the spinous process.

Each of these variations have differing compressibilities, rotational centers (upon flexion, extension, and upon lateral flexing of the spine), and movement of those centers during flex. The fore-aft length of the spinous process attachment members, of the core assembly, and the manner of attachment to the spinous processes quantitatively affect the gross support provided to an adjacent disc. Those lengths have an indirect effect on the limits of rotation.

Inter spinous process spacer variation (426) also includes relatively long upper (430) and lower (432) spinous process attachment members. The core assembly (428) is relatively short fore-and-aft, and is not adjacent either of the attachment members (430, 432). The rotational characteristics are different than the longer core assemblies.

Inter spinous process spacer variation (434) includes relatively long upper (436) and lower (438) spinous process attachment members. The core assembly (428) is relatively long fore-and-aft and extends axially for the distance between the attachment members (436, 438). These core assemblies may be designed to absorb significant amounts of compression and to allow (or not) lateral and fore-and-aft linear motions, if such is desired. Varying, e.g., the compressibility of the core also allows tailoring the rotational characteristics of the spacer, perhaps providing ease of rotation through a first portion of the rotation and more rotational difficulty through a later section.

Inter spinous process spacer variation (442) includes a relatively long upper spinous process attachment member (444) and a relatively short spinous process attachment member (446) that are offset fore-and-aft from each other. This offset, in particular, allows tailoring of the bias provided by the spacer to the adjacent spinous processes. The spinous process attachment members (444, 446) are substantially parallel each other.

Inter spinous process spacer variation (450) is similar to the spacer variation (442) discussed just above in that it includes a relatively long upper spinous process attachment member (452) and a relatively short spinous process attachment member (454) that are offset fore-and-aft from each other. In this variation, however, the spinous process attachment members (452, 454) are not parallel to each other. This combination of features allows further adjustment of incipient bias as well as providing for maintenance of, e.g., a lordotic or kyphotic angle between the upper and lower adjacent vertebrae.

Figure 14A:
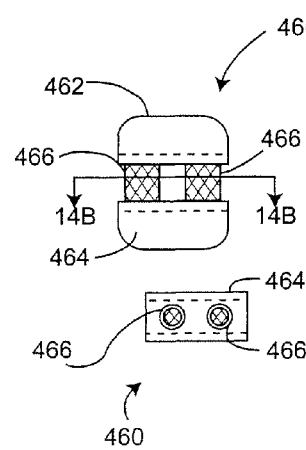
FIGS. 14A and 14B show, respectively, a side view and a top, cross-sectional view of an inter spinous process spacer variation having two core members that are offset fore-and-aft from each other along the axis of the spinous process.
Figure 14B:
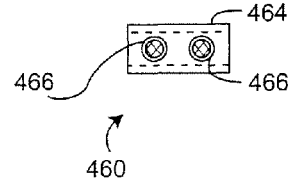

FIGS. 14A and 14B show, respectively, a side view and a top, cross-sectional view of an inter spinous process spacer variation (460) having an upper spinous process attachment member (462) and a lower spinous process attachment member (464) and two core members (466) that are offset fore-and-aft from each other along the axis of the spinous process.

FIGS. 15A-15G show an inter spinous process spacer variation (500) that is assembled during implantation and is introduced laterally into the inter spinous process space.

FIG. 15A provides a back view of the assembled inter spinous process spacer variation (500). Visible are the upper spinous process attachment member (502) and a lower spinous process attachment member (504) each respectively having a slot (506, 508) to receive a spinous process. Also visible in this back view are the core assembly (510) having an upper end plate (512), a lower plate (514), and the resilient core (516).

FIG. 15B is a back view, cross section of the upper spinous process attachment member (502) with the slot (506) for receiving the spinous process. A recess (520) in the surface of the upper spinous process attachment member (502) that is to be adjacent the upper end plate (512). The shape of recess (520) is configured to receive a cooperatively shaped end plate (512) (e.g., in FIGS. 15A and 15C) in a direction that is lateral to the slot (506) and hence lateral to the spinous process during implantation.

FIG. 15C is a back view, cross section of upper end plate (512) having a semi-dovetail catch feature (514) and a stay (516). Openings (518) for the fibers making up a fibrous component of the core assembly (of the type discussed above with regard to FIGS. 6-8) may also be seen in the cross-section.

FIG. 15D is a top view of the upper spinous process attachment member (502) shown in FIG. 15B with the slot (506) for receiving the spinous process.

FIG. 15E shows a bottom view of the upper spinous process attachment member (502) with the opening (520) for cooperatively engaging the semi-dovetail catch feature (514) and stay (516) of upper end plate (512) as shown in FIGS. 15C and 15G. Attachment member (502) includes a matching dovetail ledge (526) and an opening (526) for engaging stay (516).

FIG. 15F shows a core-side view of the end plate (512) and the openings (518) for the fibers making up a fibrous component of the core assembly (516).

FIG. 15G shows the side of the end plate (512) placed adjacent the upper spinous process attachment member (502) with the semi-dovetail catch feature (514) and stay (516). The openings (518) for the fibers making up a fibrous component of the core assembly (516) may also be seen.

The process for implanting the device shown in FIGS. 15A-15G is found in FIG. 17. However, it should be apparent that as the upper end plate (512) slides laterally adjacent the upper spinous process attachment member (502), the semi-dovetail catch feature (514) and stay (516) of upper end plate (512) slide within opening (520) in upper spinous process attachment member (502), past matching dovetail ledge (526) in attachment member (502) and into the deeper portion of the opening (520). The upper end plate (512) is then retracted, the semi-dovetail catch feature (514) engages matching dovetail ledge (524) and is pulled towards the attachment member (502). The stay member (516) also engages and enters opening (526) snapping the two parts together.

If the implanted spacer is of the design shown in FIG. 15A, a lower end plate similar to upper end plate (512) is engaging a lower spinous process attachment member similar to the upper spinous process attachment member (502) as the top portions of the spacer are being similarly engaged.

Other mechanisms for latching or otherwise securing laterally introduced end plates to spinous process attachment members may be used in our dynamic spacers.

FIG. 16 provides a schematic procedure for implanting by a lateral approach one version of our dynamic spacer using, as an example, the spacer found in FIGS. 15A-15G.

In step (a.), two adjacent spinal processes (600, 602) have been prepared to allow access to the space between them. Two spinous process attachment components (604, 606) removably attached to instrumentation (608) configured to allow movement of the two attachment components (604, 606) laterally into the inter spinous process space and then to separate those two attachment components (604, 606) to engage the spinous processes.

In step (b.), a compressible core (610) having instrumentation (612) to allow insertion and retraction of the core (610), is shown approaching the space between the two spinous process attachment components (604, 606). The attachment components instrumentation holds the two attachment components (604, 606) in position during insertion of the core (610). In this example, the manner of latching the core (610) to the two attachment components (604, 606) involves the semi-dovetail and stay shown in FIGS. 15A-15G.

In step (c.), the core instrumentation (612) has pushed the core (610) past the engagement point and is retracting the core (610) to latch the end plates of the core (610) to the two attachment components (604, 606).

In step (d.), the core (610) is fixed to the two attachment components (604, 606) and the spacer device has been implanted. The two implantation instruments (608, 610) have been released from the two attachment components (604, 606) and the core (610) and are being withdrawn.

FIG. 17 provides a schematic procedure for implanting a version of our dynamic spacer by a posterior approach using, as an example, the spacer found in FIG. 9. FIG. 17 provides a side view.

In step (a.), a variation of our inter spinous process spacer (620) having an upper spinous process attachment member (622), a lower spinous process attachment member (624), and a compressible core assembly (626) is shown approaching the space between an upper spinous process (630) and a lower spinous process (632). Instrumentation (628) attached to the two attachment members (620, 624) is configured to compress the spacer (620) during implantation.

In step (b.), the inter spinous process spacer (620) has been released by the instrumentation (628) and the spacer (620) has expanded to engage the spinous processes (630, 632). The spacer is now implanted.

I claim:

1. An inter spinous process, dynamic stabilizing device interposable between first and second spinous processes associated with first and second vertebrae, where the second vertebra is adjacent said first vertebra in a human spine, said first and second vertebrae having facet joints and foramenal spaces, said device comprising:
   a.) at least one central core assembly, comprising,
      i.) first and second end plates,
      ii.) at least one compressible core member positioned between and adjacent to said first and second end plates, and
      iii.) at least one fiber extending between and engaged with said first and second end plates, wherein the at least one fiber extends from the first end plate to the second end plate without contacting the first and second spinous processes and back to the first end plate without contacting the first and second spinous processes,
   b.) bone attachment members, each bone attachment member including a pillar extendable from and attachable to said first and second end plates, respectively, the bone attachment members being attachable to said first and second spinous processes, respectively, wherein the pillars of the bone attachment members are configured, after implantation of this stabilizing device between the first and second spinous processes, to space at least one of the first and second end plates from the first and second spinous processes.

2. The stabilizing device of claim 1 where the at least one central core assembly is configured to stabilize the spacing between the first spinous process and the second spinous process, to absorb compression, to permit rotation between the first and second vertebrae, and to permit lateral bending between the first and second vertebrae.

3. The stabilizing device of claim 1 wherein the stabilizing device is sized such that, when implanted between the first spinous process and the second spinous process, the stabilizing device restores a posterior tension band between first and second vertebrae, realigns facets associated with the first and the second vertebrae, and restores a foramenal height associated with the first and the second vertebrae.

4. The stabilizing device of claim 1 wherein the at least one compressible core member comprises one or more polymeric materials.

5. The stabilizing device of claim 1 wherein the stabilizing device comprising bone attachment members attached to said first and second end plates is configured to be implanted between said first and second spinous processes by a posterior approach.

6. The inter spinous process stabilizer of claim 1 wherein the bone attachment members are configured to be attached to said first and second end plates in situ, after such bone attachment members are attached to said first and second spinous processes.

7. The inter spinous process stabilizer of claim 1 wherein the first and second end plates each have a periphery and the at least one fiber extending between and engaged with said first and second end plates is wound around the periphery of each of the first and second end plates.

8. The inter spinous process stabilizer of claim 1 wherein the first and second end plates each have an interior surface adjacent to the at least one compressible core member and wherein those interior surfaces are substantially flat.

9. The inter spinous process stabilizer of claim 1 wherein the bone attachment members each further comprise at least one bone fixation element.

\* \* \* \* \*